United States Patent
Kim et al.

(10) Patent No.: US 11,154,705 B2
(45) Date of Patent: Oct. 26, 2021

(54) OPTICAL SENSOR ARRAY-BASED SUB-TYPE ARTIFICIAL RETINA DEVICE, AND METHOD FOR DRIVING ARTIFICIAL RETINA DEVICE

(71) Applicants: GACHON UNIVERSITY OF INDUSTRY-ACADEMIC COOPERATION FOUNDATION, Seongnam-si (KR); KOREA UNIVERSITY RESEARCH AND BUSINESS FOUNDATION, Seoul (KR)

(72) Inventors: Jungsuk Kim, Yongin-si (KR); Seong-woo Kim, Seoul (KR)

(73) Assignees: GACHON UNIVERSITY OF INDUSTRY-ACADEMIC COOPERATION FOUNDATION, Seongnam-si (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 255 days.

(21) Appl. No.: 16/328,713

(22) PCT Filed: Aug. 31, 2017

(86) PCT No.: PCT/KR2017/009571
§ 371 (c)(1),
(2) Date: Feb. 26, 2019

(87) PCT Pub. No.: WO2018/044106
PCT Pub. Date: Mar. 8, 2018

(65) Prior Publication Data
US 2019/0209833 A1    Jul. 11, 2019

(30) Foreign Application Priority Data

Aug. 31, 2016 (KR) .................. 10-2016-0111594

(51) Int. Cl.
*A61F 2/14* (2006.01)
*A61N 1/05* (2006.01)
(Continued)

(52) U.S. Cl.
CPC .............. *A61N 1/0543* (2013.01); *A61F 2/14* (2013.01); *A61F 9/08* (2013.01); *A61N 1/04* (2013.01);
(Continued)

(58) Field of Classification Search
CPC .......... A61N 1/0543; A61N 1/04; A61N 1/05; A61N 1/08; A61N 1/36; A61N 1/36046;
(Continued)

(56) References Cited

U.S. PATENT DOCUMENTS 6,458,157 B1 * 10/2002 Suaning .................... A61F 2/14
    623/6.63
2003/0014089 A1 * 1/2003 Chow ................ A61N 1/36046
    607/54
(Continued)

FOREIGN PATENT DOCUMENTS

JP    2012-115545 A    6/2012
JP    5443989 B2    3/2014
(Continued)

OTHER PUBLICATIONS

Goetz GA, Palanker DV. Electronic approaches to restoration of sight. Rep Prog Phys. 2016;79(9):096701. doi:10.1088/0034-4885/79/9/096701.

*Primary Examiner* — Ankit D Tejani
*Assistant Examiner* — Joshua Brendon Solomon
(74) *Attorney, Agent, or Firm* — Workman Nydegger

(57) ABSTRACT

A subretinal prosthetic device includes a substrate provided under a retina, a return electrode for receiving a current such that a ground is formed on the substrate, a plurality of
(Continued)

stimulating electrodes provided on the substrate and for generating an active potential to an optic nerve in response to external visual information projected onto the retina, and a switch for controlling the current between each of the plurality of stimulating electrodes and the return electrode. The switch is connected between the plurality of stimulating electrodes and the return electrode to ground the plurality of stimulating electrodes to the return electrode in response to an on or off control signal.

14 Claims, 11 Drawing Sheets

(51) Int. Cl.
    *A61N 1/08*     (2006.01)
    *A61N 1/36*     (2006.01)
    *A61N 1/04*     (2006.01)
    *A61F 9/08*     (2006.01)
    *G01J 1/44*     (2006.01)

(52) U.S. Cl.
CPC ................ *A61N 1/05* (2013.01); *A61N 1/08* (2013.01); *A61N 1/36* (2013.01); *A61N 1/36046* (2013.01); *A61N 1/36125* (2013.01); *A61N 1/36128* (2013.01); *G01J 1/44* (2013.01)

(58) Field of Classification Search
CPC ... A61N 1/36125; A61N 1/36128; A61F 2/14; A61F 9/08; G01J 1/44
See application file for complete search history.

(56) References Cited

U.S. PATENT DOCUMENTS

| | | |
|---|---|---|
| 2006/0184245 A1 | 8/2006 | Graf et al. |
| 2006/0241753 A1 | 10/2006 | Suaning et al. |
| 2011/0082383 A1* | 4/2011 | Cory .................... A61B 5/0536 600/547 |
| 2014/0330343 A1 | 11/2014 | Suaning |
| 2016/0082250 A1* | 3/2016 | Matteucci .......... A61N 1/36164 607/54 |

FOREIGN PATENT DOCUMENTS

| | | |
|---|---|---|
| KR | 10-2003-0003727 A | 1/2003 |
| KR | 10-0485054 B1 | 10/2005 |
| KR | 10-2006-0018901 A | 3/2006 |
| KR | 10-1246336 B1 | 3/2013 |

* cited by examiner

[FIG. 1]
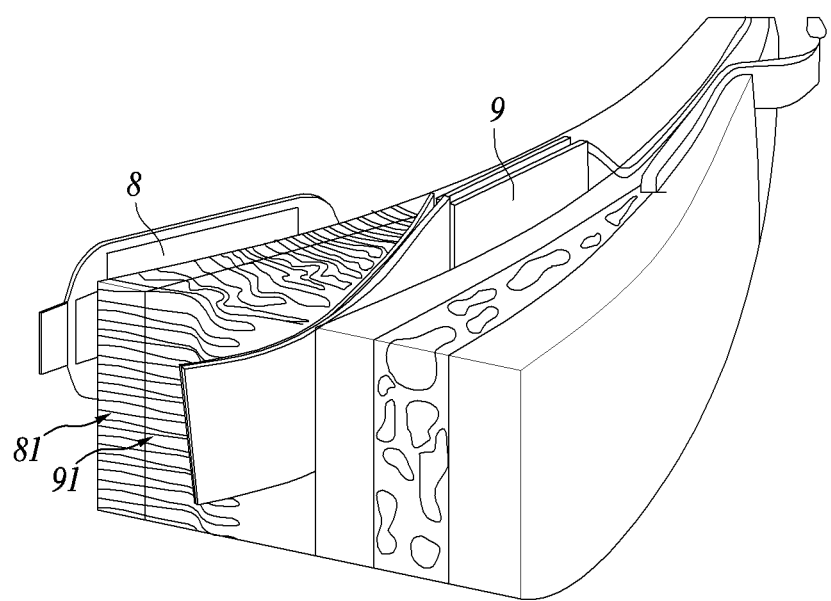

[FIG. 2]
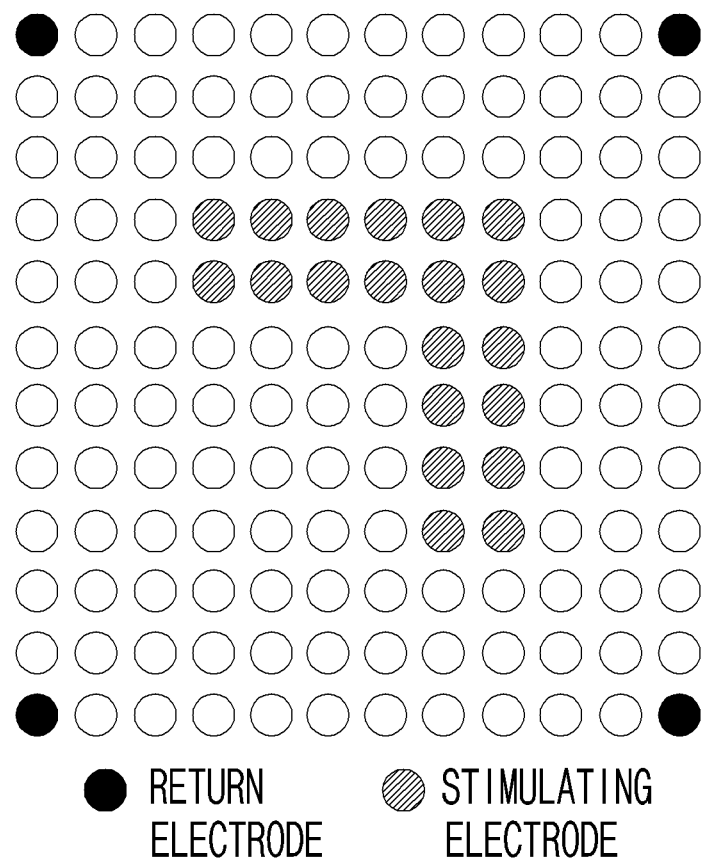

[FIG. 3]
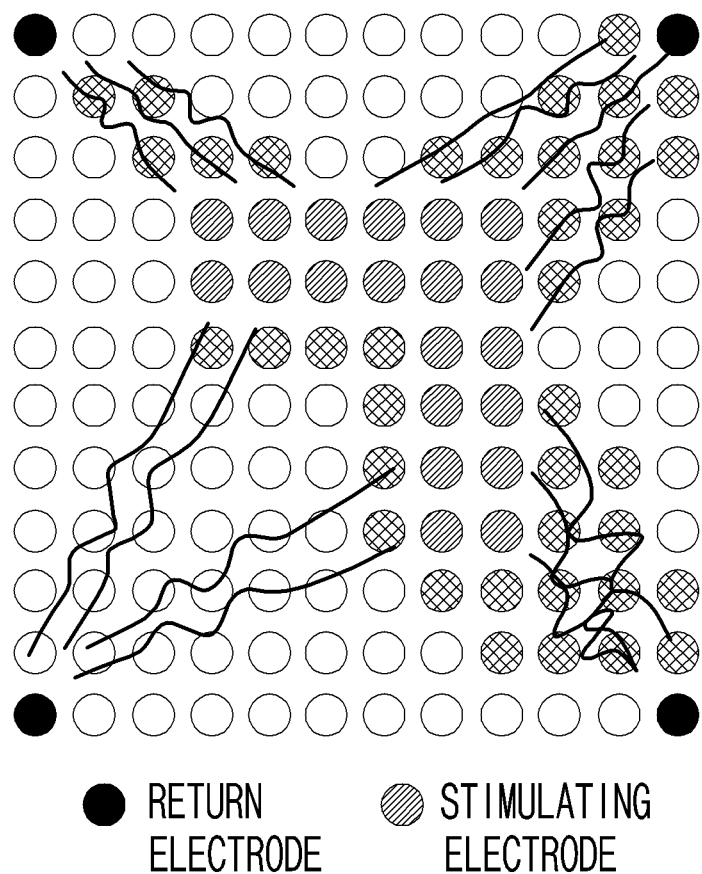

[FIG. 4]
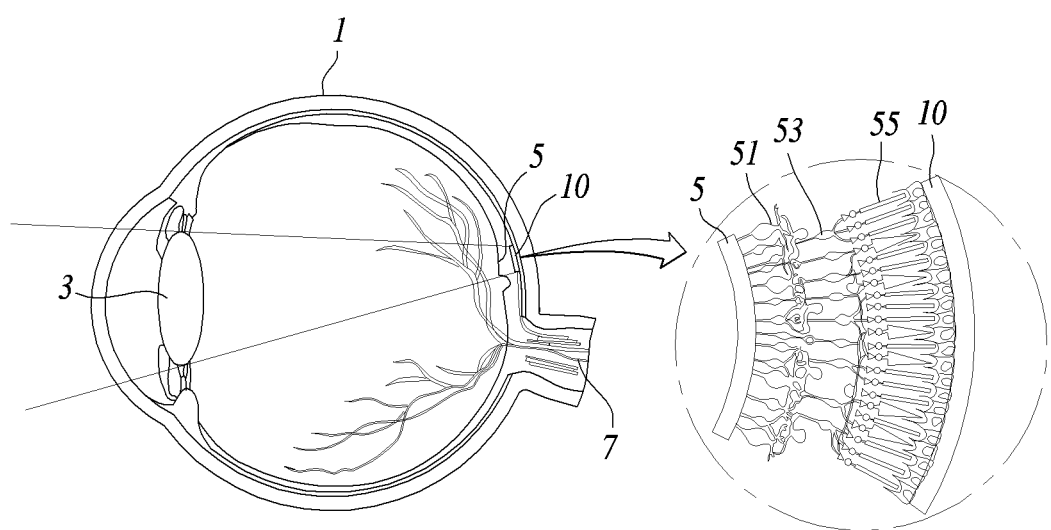

[FIG. 5]
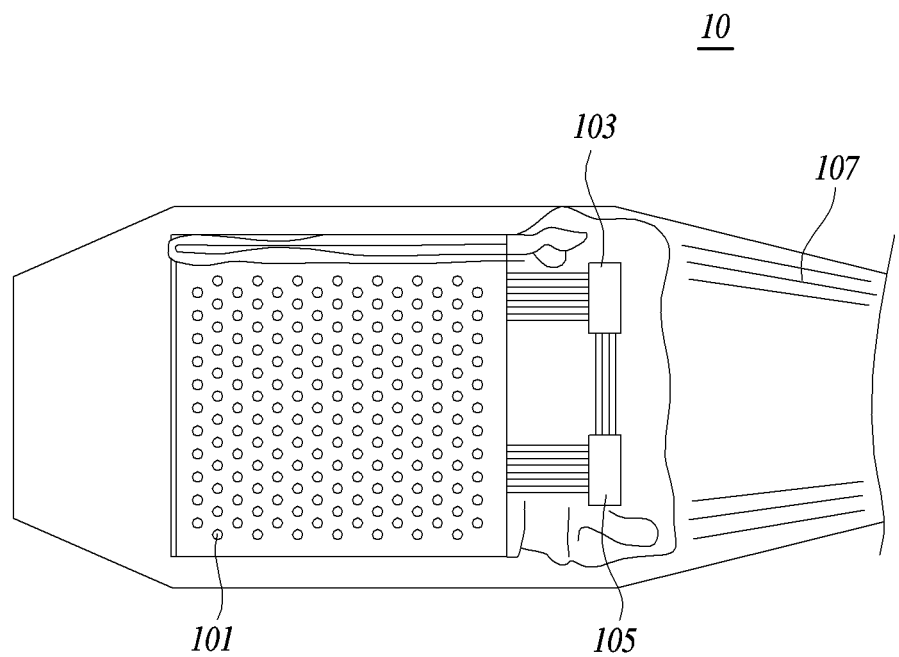

[FIG. 6]
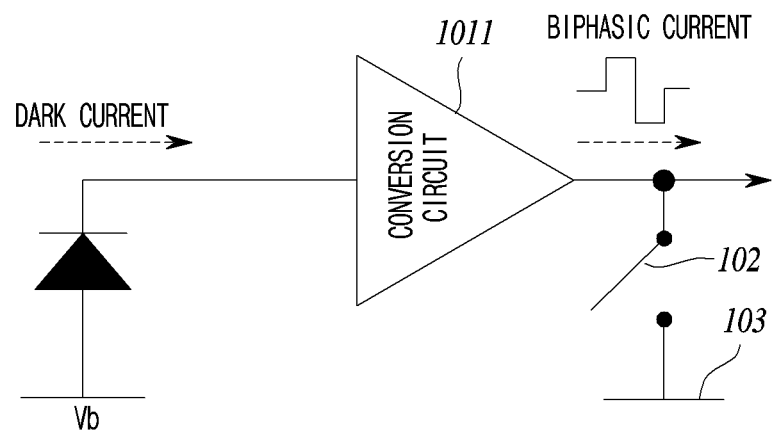

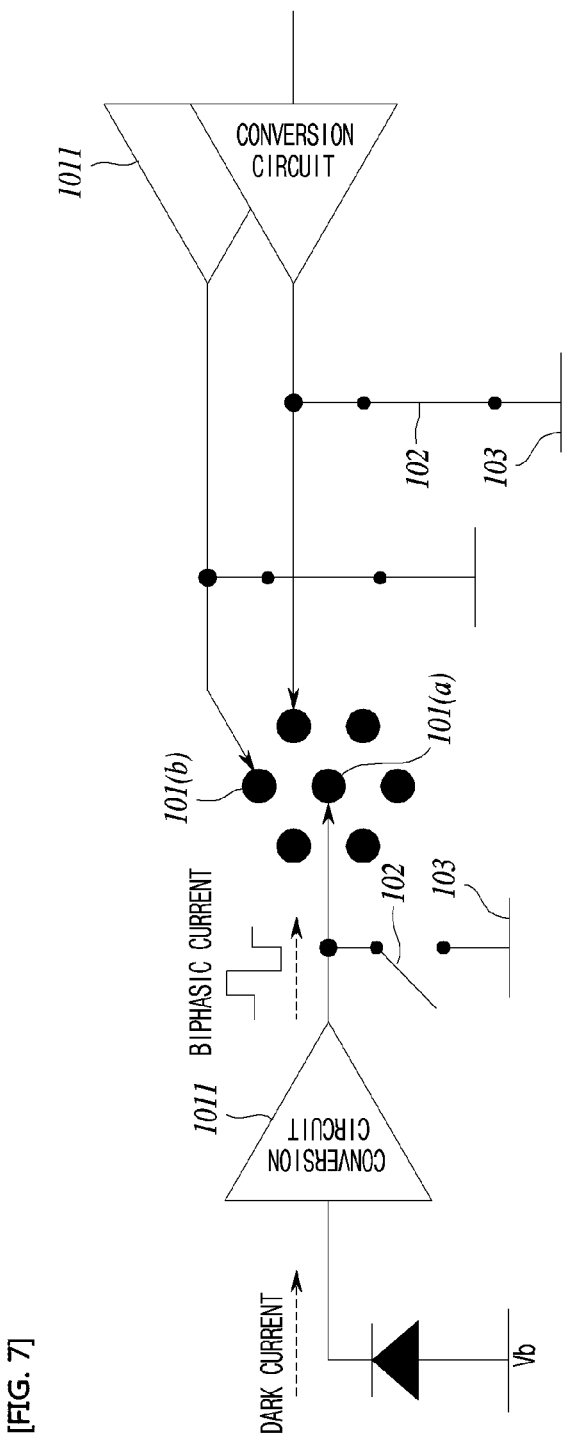

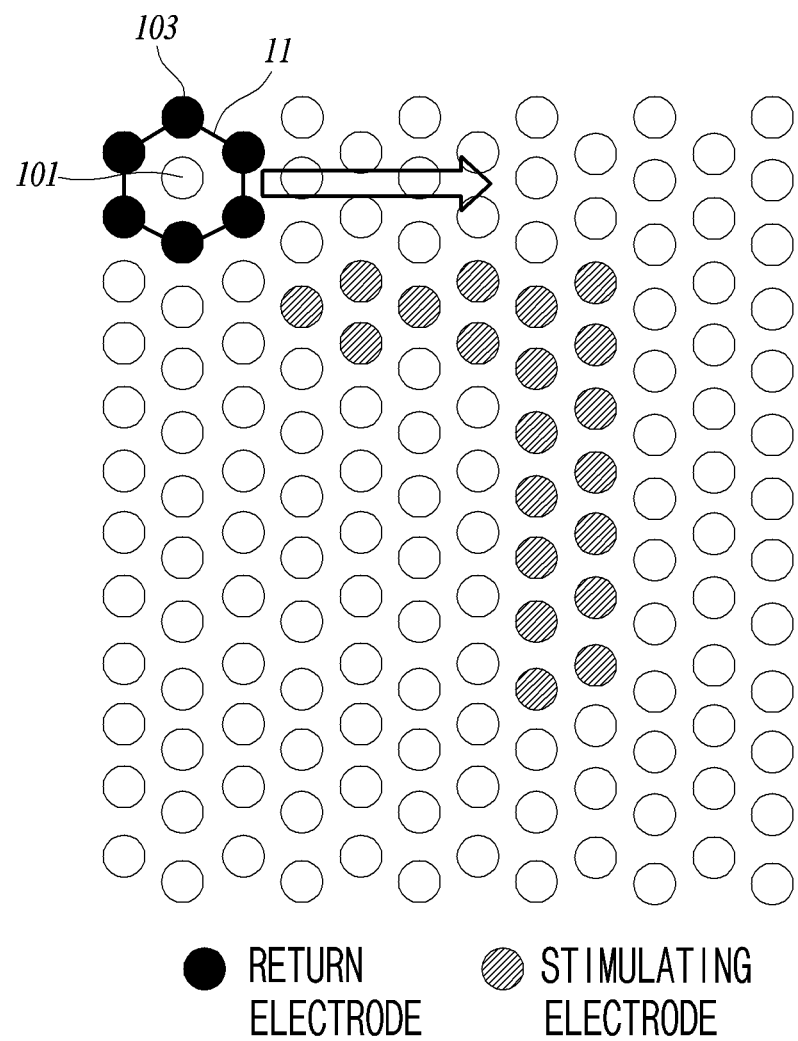
[FIG. 8]

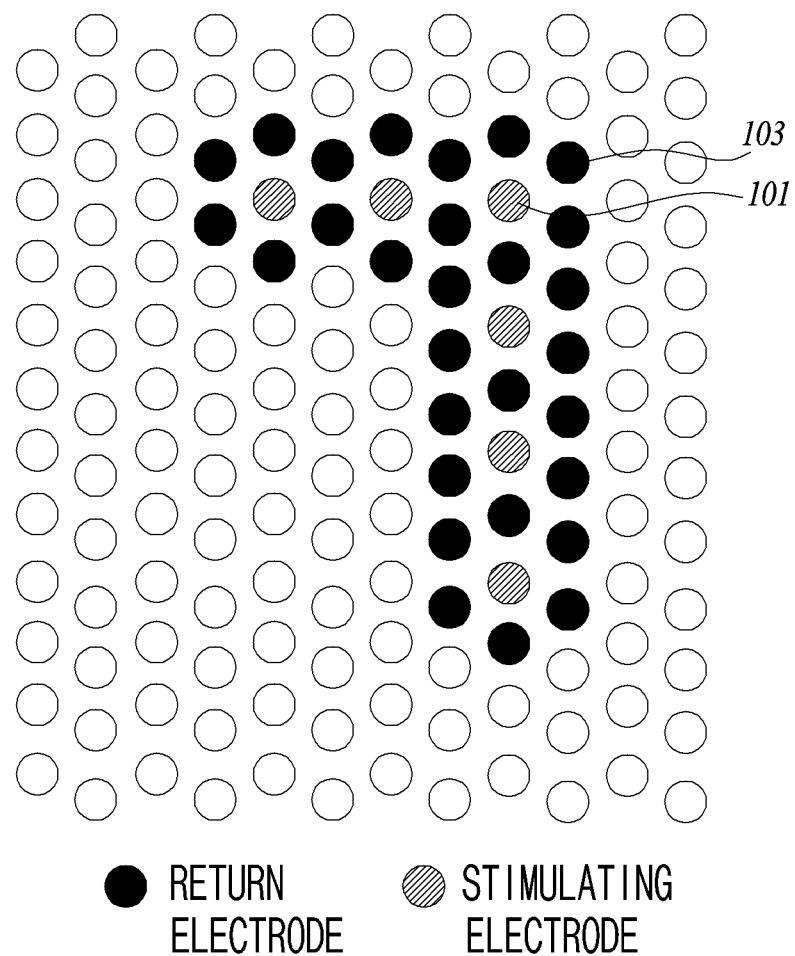

[FIG. 10]
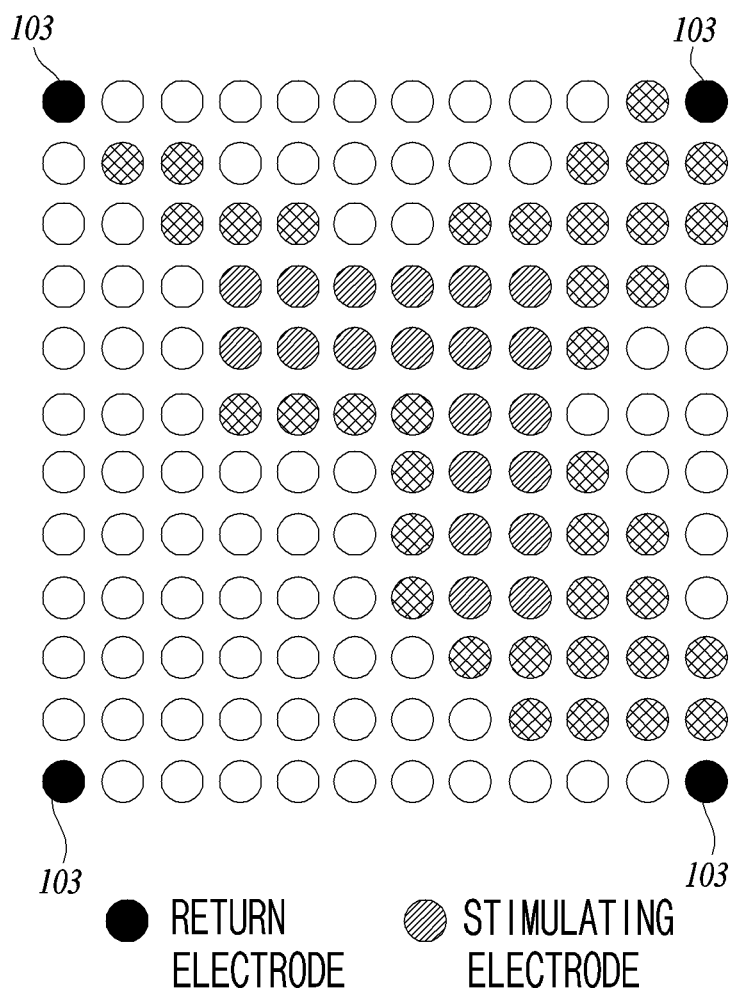

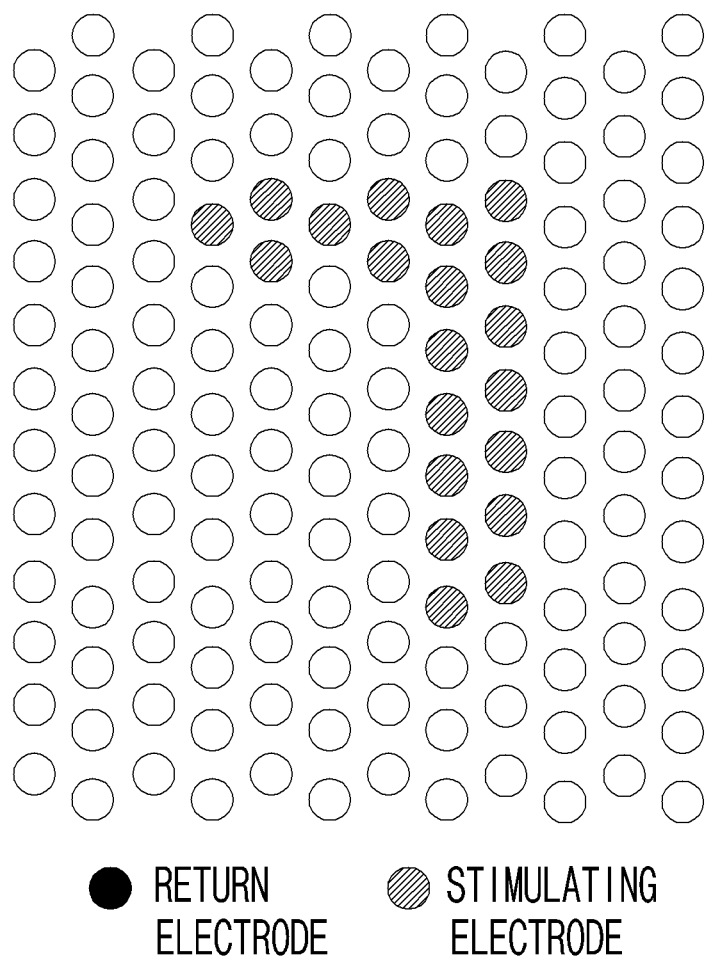
[FIG. 11]

OPTICAL SENSOR ARRAY-BASED SUB-TYPE ARTIFICIAL RETINA DEVICE, AND METHOD FOR DRIVING ARTIFICIAL RETINA DEVICE

CROSS-REFERENCE TO RELATED APPLICATIONS

This application claims priority to PCT Application No. PCT/KR2017/009571 filed Aug. 31, 2017, entitled "Optical Sensor Array-based Sub-Type Artificial Retina Device, and Method for Driving Artificial Retina Device," which claims the benefit of and priority to Korean Patent Application No. 10-2016-0111594, filed on Aug. 31, 2016. All the aforementioned applications are incorporated by reference herein in their entirety.

BACKGROUND OF THE INVENTION

1. Field of the Invention

The present disclosure relates to a subretinal prosthetic device, which is implanted in a photoreceptor cell layer of a retina, in particular, under the retina, to induce an electrical impulse, thereby restoring vision to the user, and a driving method for the same.

2. Description of the Related Art

The retina is an important nerve tissue for converting, into electrical signals, external images received through the cornea and the lens of the eye and transmitting the electrical signals to the brain. The width of the retina is about 6.25 $cm^2$, and there are about 100 million photoreceptor cells in the retina. The rod cells, which are the majority of the photoreceptor cells, convert images into electrical signals. These signals enter the optic nerve and are transmitted to the brain at a speed of about 480 km/h. The brain interprets minute electrical signals to identify images, thereby determining objects. The retina is one of the tissues with the largest blood supply per unit area and requires many energy sources, and the wastes generated as by-products of the chemical action must be removed smoothly. For any reason, abnormalities in retinal or choroidal blood vessels cause those in the retina, resulting in various diseases.

As a retinal disease, retinitis pigmentosa (RP) is a progressive retinal degenerative disease caused by dysfunction of the photoreceptors distributed in the retina. The photoreceptors of the retina and the retinal pigment epitheliums are the main lesions. The RP is characterized by appearing in both eyes. The prevalence rate of RP is reported to be one in 5,000 people through the world. As another retinal disease, age-related macular degeneration (AMD) is one of the three blindness diseases, and the prevalence rate is greatly on the rise due to the rapid aging of the population. Patients with AMD often have a relatively short-term deterioration in vision, unlike those with low vision due to RP. The degree of actual life impairment and psychological atrophy resulting from the eyes of AMD patients have been reported to be greater than those due to other diseases.

To treat patients with blindness, various treatments such as gene therapy, stem cell therapy, and drug therapy have been attempted. However, most of the patients with blindness have already had the damaged retinal photoreceptor cell layers that have gone beyond the time of gene therapy or drug therapy. Only the photoreceptor cell layer, which is the outer layer of the retina, is damaged, in the case of geriatric diseases such as RP and AMD, so that there is a possibility of visual recovery if the function of the photoreceptor cell layer is replaced with new one. Thus, retinal prostheses that induce electrical impulses to the photoreceptor cell layers of the retinas of blind patients to restore the vision are promising as a new treatment.

Referring to FIG. 1, a retinal prosthesis may be divided into epirential and subretinal prostheses. The epirential prosthesis is positioned in front of the retina and indicated by reference sign 8 in FIG. 1. The subrential prosthesis is positioned in a photoreceptor cell layer in rear of the retina and indicated by reference sign 9 in FIG. 1. The epiretinal prosthesis stimulates the ganglion cell layer among the retinal cells, and the subrential prosthesis stimulates the bipolar cell layer therebehind. A nerve cell stimulator is positioned in front of the retina, so that intermediate signal processing of the nerve cells included in the inner layer of the retina does not proceed. Thus, the epiretinal prosthesis has an additional external camera. The external camera is mounted on glasses, and the image information obtained from the external camera reaches a microelectrode array in the eye wirelessly through an induction coil to stimulate the retinal ganglion cells directly without the intermediate signal processing of the nerve cells included in the inner layer of the retina. Meanwhile, patients have different threshold values in response to electrical impulses, and the magnitudes of electrical impulses to be applied to a damaged site of the retinal cells are also different from each other. The epiretinal prosthesis allows an external image processor to control electrodes independently. Thus, the epiretinal prosthesis can change the magnitudes of electrical impulses arbitrarily according to patients or damaged sites. As the related art, *Argus®* II (Second Sight) being sold in the U.S. can control 64 electrodes independently and also control the magnitudes of electrical impulses generated by electrodes, respectively. Merely, since the epiretinal prosthesis has a very thin and fragile retina, it is difficult to fix the electrodes thereto. Further, since the epiretinal prosthesis is positioned inside the retina, the epiretinal prosthesis is likely to be intravitreally exposed, and since the epiretinal prosthesis is enclosed by fibrous tissues, the epiretinal prosthesis cannot transmit electrical impulses. In addition, when the epiretinal prosthesis provides electrical impulses to the upper surface of the retina, it is difficult to stimulate the retinal nerve fiber layer to spread signals or to stimulate the multilayer cells of the retina at a time to increase a spatial resolution. Since the epiretinal prosthesis cannot utilize the intermediate signal processing, the shape of a stimulating electrode grid and the shape actually felt by patients may be different. Therefore, customized image processing suited to individual patients is required. As a result, the epiretinal prosthesis requires various components and a signal transmission unit for connecting the components, compared to the subrential prosthesis.

The subrential prosthesis has a photodiode array positioned in the photoreceptor cell layer, which is disposed below the retina cell layer, as in FIG. 1. The subrential prosthesis is designed to simply replace the function of the photoreceptors and makes the bipolar cells a primary object to be electrically stimulated. To this end, the subrential prosthesis is designed to integrate a photodiode for detecting light with a stimulating electrode and allow an electrical current from the photodiode to directly flow into the stimulating electrode to stimulate the ganglion cells. The photodiode array performs a function similar to that of complementary metal-oxide semiconductor (CMOS) image sensors. The magnitudes of dark currents generated by photodiode cells according to the intensity of light are different, and the dark currents are changed to biphasic current pulses that serve as an active potential through a conversion circuit. The subrential prosthesis uses a visual pathway of the related art through information processing of the bipolar cells and the inner layer of the retina to enable the user to have a natural feeling in recognizing an object. Moreover, since a microelectrode array is inserted into the eye, the subrential prosthesis enables a natural eye movement, which is physiological and natural when compared to a system that has a small camera mounted on glasses and allows the user to turn the head rather than the eyes in the direction of the object in order to look at and recognize the object. In addition, since the subrential prosthesis among the retinal prostheses ever made has the greatest number of pixels created by a subretinal stimulation method, the possibility of realizing high resolution is suggested.

It has been reported that the Alpha IMS model as the related art, which was successfully commercialized by Retina Implant in Germany, had an array of 1,500 photodiodes and a biphasic current generation array matched thereto, but had an actual resolution lower than the resolution of a 63-channel epiretinal prosthesis in a clinical test. When the epiretinal prosthesis stimulates the cell layer, an image captured from the camera is converted into a digital signal through image processing, the digital signal is changed to a serial digital signal through encoding, and the serial digital signal is transmitted to the epiretinal prosthesis. A decoder of the epiretinal prosthesis analyzes the packet of a digital signal received from the outside and sends instruction signals to stimulators sequentially. The stimulators, having received the instruction signals, generate a biphasic current, and the output terminals of the other stimulators waiting for the instruction signals are shorted with a return electrode to prevent remaining electrical charges from being widely spread.

In contrast, the photodiode array of the subrential prosthesis receives light simultaneously and generates biphasic currents at the same time. Meanwhile, the subrential prosthesis has a return electrode that is positioned away from the end of a chip or the electrode array and serves as a ground. In general, the return electrode is positioned in the corner of a quadrangular chip to serve as a ground. When a plurality of stimulating electrodes in a predetermined area are simultaneously stimulated in such situations, currents stimulate the bipolar cells of the retina that must not be stimulated while flowing into the return electrode, and thus crosstalk by which images blur occurs. FIGS. 2 and 3 illustrate a photodiode array for describing such a phenomenon.

It is assumed that the shape that the user desires to recognize is "L" in FIGS. 2 and 3. For example, the shape "L" passes through the intermediate cell layer of the retina to reach the subrential prosthesis in rear thereof, and simultaneous stimuli are input in the "L" shape to an array of photodiodes arranged in a plurality of pixels (for example, 1,000 pixels). Stimulating electrodes output a biphasic current in the "L" shape. While currents flow into a return electrode (a ground electrode) that must be provided somewhere on a substrate as in FIG. 3, the currents stimulate unintended bipolar cells, and thus the user recognizes that the "L" shape blurs. For this reason, it is pointed out that the user feels that the resolution of a 1,000-pixel subrential prosthesis is similar to that of a 64-pixel epiretinal prosthesis.

Thus, the present applicant has devised a circuit structure and a control method that can solve the above-mentioned image blurring issue of the subrential prosthesis. A preceding patent, in which an array structure or an electrode structure capable of solving the above issue of the subrential prosthesis is suggested, has not been searched, and a related patent is disclosed in Korean Patent Registration No. 10-1246336.

SUMMARY OF THE INVENTION

Embodiments of the present invention are directed to providing a retinal prosthetic device, which allows a current flowing into a return electrode not to stimulate an unintended bipolar cell, thereby significantly reducing crosstalk.

Embodiments of the present invention are also directed to providing a retinal prosthetic device, which may provide a resolution that is optimized to an array of photodiodes and stimulating electrodes that may be provided in more than or equal to 1,000 pixels.

According to an aspect of the present invention, there is provided a subrential prosthesis including: a substrate provided under a retina; a return electrode for receiving a current such that a ground is formed on the substrate; a plurality of stimulating electrodes provided on the substrate and for generating an active potential to an optic nerve in response to external visual information projected onto the retina; and a switch for controlling the current between each of the plurality of stimulating electrodes and the return electrode, and the switch is connected between the plurality of stimulating electrodes and the return electrode to ground the plurality of stimulating electrodes to the return electrode in response to an on or off control signal.

The substrate may have the plurality of stimulating electrodes arranged in a zigzag pattern in an X- or Y-axis column.

The stimulating electrode may output a biphasic current having two phases of a negative pole and a positive pole for balancing of an electric charge transferred to the optic nerve.

The switch may allow an output line, through which an impulse of the stimulating electrode is outputted, to branch to be connected to the return electrode.

The switch may be provided as a plurality of switches, which may be connected to the plurality of stimulating electrodes, respectively.

The substrate may allow a portion of the plurality of stimulating electrodes, which are adjacent to any one of the plurality of stimulating electrodes for generating the active potential, to be operated as the return electrode.

The adjacent stimulating electrodes may be a plurality of stimulating electrodes spaced apart from the one stimulating electrode at the same distances around the one stimulating electrode for generating the active potential.

The adjacent stimulating electrodes may form a hexagonal array around the one stimulating electrode for generating the active potential.

The substrate may further include a control module for setting, as a scanning array, a portion of the plurality of stimulating electrodes included in a portion of a region in which the plurality of stimulating electrodes are arranged, switching from the portion of the plurality of stimulating electrodes of the scanning array to the return electrode, and setting, as the scanning array, another portion of the plurality of stimulating electrodes included in another portion of the region.

The control module may set the scanning array at a frequency of higher than or equal to 50 Hz.

The scanning array may be set as the portion of the plurality of stimulating electrodes spaced apart from any one of the plurality of stimulating electrodes at the same distances around the one stimulating electrode to form a hexagonal array.

The control module may perform control such that the same stimulating electrode does not continue to be selected during the setting of the scanning array.

According to another aspect of the present invention, there is provided a method of driving a subretinal prosthetic device including: (a) setting, as a scanning array, a portion of a plurality of stimulating electrodes included in a portion of a region in which the plurality of stimulating electrodes are arranged, the plurality of stimulating electrodes being provided on a substrate under a retina to generate an active potential to an optic nerve in response to external visual information projected onto the retina; (b) connecting the portion of the plurality of stimulating electrodes of the scanning array to a return electrode for receiving a current; and (c) setting, as the scanning array, another portion of the plurality of stimulating electrodes included in another portion of the region in which the plurality of stimulating electrodes are arranged, and operations (a) to (c) are repeated at a frequency of higher than or equal to 50 Hz.

Operation (a) may set, as the scanning array, the portion of the plurality of stimulating electrodes spaced apart from any one of the plurality of stimulating electrodes at the same distances around the one stimulating electrode, and the scanning array may be a hexagonal array.

Operation (c) may set the scanning array such that the portion of the plurality of stimulating electrodes selected in operation (a) do not continue to be selected.

According to the present invention, an array is formed to have a structure in which a switch is connected to a plurality of stimulating electrodes so that the stimulating electrodes may be operated as a return electrode. In particular, hexagonal stimulating electrodes set as a scanning array operate as the return electrode, and the scanning array is moved at a speed of 50 Hz that is difficult for the user to recognize. For example, the return electrode is scanned in a flexible manner rather than a stationary manner. In this case, when the stimulating electrodes positioned in the center of the scanning array recognize external light, a biphasic current flows into the adjacent return electrode of the scanning array even when the biphasic current is outputted not to unnecessarily stimulate bipolar cells around the stimulating electrodes. In this manner, the present invention may provide a switch structure of the stimulating electrodes and a control method for the scanning array, which may significantly reduce crosstalk and provide a resolution that is optimized to an array of photodiodes and stimulating electrodes that may be provided in more than or equal to 1,000 pixels.

BRIEF DESCRIPTION OF THE DRAWINGS

The above and the other objects, features and other advantages of the present invention will be more clearly understood from the following detailed description taken in conjunction with the accompanying drawings, in which:

FIG. 1 illustrates a retinal prosthesis;

FIGS. 2 and 3 are supplemental views describing a subretinal prosthetic device of the related art;

FIG. 4 is a view illustrating the shape of an eye in which a subretinal prosthetic device according to an embodiment of the present invention is implanted;

FIG. 5 illustrates the subretinal prosthetic device according to an embodiment of the present invention;

FIG. 6 illustrates a circuit diagram of a stimulating electrode of the subretinal prosthetic device according to an embodiment of the present invention;

FIG. 7 illustrates a scanning array of the subretinal prosthetic device according to an embodiment of the present invention;

FIG. 8 is an example illustrating an operation of the scanning array of the subretinal prosthetic device according to an embodiment of the present invention;

FIG. 9 illustrates an arrangement of a stimulating electrode and a return electrode recognized by the user in the example of FIG. 8; and FIGS. 10 and 11 illustrate a difference between return methods using the scanning array.

DESCRIPTION OF THE PREFERRED EMBODIMENTS

Hereinafter, specific embodiments of the present invention will be described in detail with reference to the accompanying drawings. The present invention should not be construed as limited to the embodiments set forth herein. Like reference numerals in the drawings denote members for performing substantially the same function.

The objects and effects of the present invention can be naturally understood or clarified by the following description and are not limited by the following disclosure. In describing the present invention, if it is determined that a detailed description of known techniques associated with the present invention may unnecessarily obscure the gist of the invention, the detailed description will be omitted.

FIG. 4 is a view illustrating the shape of an eye in which a subretinal prosthetic device 10 according to an embodiment of the present invention is implanted. The eye has a structure including a retina 5, a nerve tissue 7, a choroid, a sclera, a cornea 1, a pupil 3, an iris, and a ciliary body. As described above, the subretinal prosthetic device 10 is positioned in rear of the retina 5. The retina 5 has a multilayer structure of a ganglion cell, an amacrine cell, a bipolar cell, a horizontal cell, rod and cone cells, and a pigment epithelium. For convenience of explanation, the retina 5 is divided into a ganglion cell layer 51, a bipolar cell layer 53, and a rod cone layer 55 in FIG. 4. The subretinal prosthetic device 10, according to this embodiment, may be positioned to stimulate the rod cone layer 55. All of the ganglion cell layer 51, the bipolar cell layer 53, and the rod cone layer 55 are a transparent cell layer, and thus light incident onto the retina is projected thereto to reach the subretinal prosthetic device 10. The subretinal prosthetic device 10 may use intermediate signal processing of nerve cells included in an inner layer of the retina as is. In the intermediate signal processing, the subretinal prosthetic device 10 according to this embodiment provides high-resolution visual information to the user by preventing a stimulating electrode responding to external visual information from unnecessarily stimulating the bipolar cell layer 53. Hereinafter, the configuration of the subretinal prosthetic device 10 is as follows.

FIG. 5 illustrates the subretinal prosthetic device 10 according to an embodiment of the present invention.

Referring to FIG. 5, the subretinal prosthetic device 10 may include a substrate, stimulating electrodes 101, a return electrode 103, a control module 105, and a switch 102 (refer to FIG. 6).

The substrate is provided under the retina. The substrate may have photodiodes, which are optical sensors, the stimulating electrodes, the return electrode, the control module, and power coils 107. The substrate may have flexibility. The photodiodes and the stimulating electrodes corresponding thereto are disposed on the substrate, and the size of the substrate may be designed with consideration of the number of the stimulating electrodes mounted thereon. In general, the substrate may receive the stimulating electrodes more than or equal to 1,000 to ensure a sufficient resolution. The substrate may have the stimulating electrodes 101 arranged in a zigzag pattern in an X- or Y-axis column. Each of the photodiodes responds to externally incident light, and each of the stimulating electrodes outputs a current by using a signal from the photodiode. In the present specification, the terms are not separately used in consideration of the photodiode and the stimulating electrode being provided as a module, and an arrangement of the stimulating electrodes 101 may stand for that of the photodiodes.

Referring to FIG. 5 as one feature of this embodiment, the substrate has the stimulating electrodes 101 arranged in the zigzag pattern on at least one of an X- or Y-axis. The arrangement of the stimulating electrodes 101 is provided to form a scanning array 11 as a hexagonal structure and is an appropriate structure for forming the return electrode 103 as close to the stimulating electrodes 101 responding to the external visual information as possible. The substrate allows a portion of the plurality of stimulating electrodes, which are adjacent to any one of the plurality of stimulating electrodes for generating an active potential, to be operated as the return electrode 103, the return electrode 103 is not stationarily formed, and the stimulating electrodes 101 are operated as the return electrode 103 in response to a control signal. In this regard, the features will be detailed in FIGS. 8 and 9.

The return electrode 103 receives the current such that a ground is formed on the substrate. In this embodiment, the return electrode 103 may be provided as a capacitor having a large capacitance. The return electrode 103 is formed in a region of the substrate and may also be provided in a position spaced apart from that of the array of the stimulating electrodes 101.

The stimulating electrodes 101 are provided on the substrate and generate the active potential to an optic nerve 7 in response to the external visual information projected onto the retina. The stimulating electrodes 101 form the array. As described above, the stimulating electrodes 101 are arranged in the zigzag pattern on the at least one of the X- or Y-axis. The number of the stimulating electrodes 101 is the same as an indicator indicating a resolution at which the user recognizes the external visual information, and the external visual information applies a simultaneous impulse in a shape corresponding to the arranged stimulating electrodes 101.

The stimulating electrode 101 may be connected to a CMOS image sensor or the photodiode to be constructed as a module, and, when the photodiode recognizes a photon to output a dark current, the outputted dark current is converted into a current signal suitable for the active potential through a conversion circuit 1011 of the stimulating electrode 101.

The stimulating electrode 101 may output a biphasic current having two phases of a negative pole and a positive pole for balancing of an electric charge transferred to the optic nerve. In this embodiment, the stimulating electrode 101 may output a balanced biphasic current such that a negative electrical charge and a positive electrical charge are offset by each other to prevent an electric charge having one polarity from being accumulated in the optic nerve 7. The conversion circuit 1011 of the stimulating electrode 101, outputting the active potential as the biphasic current, may be used as a circuit structure of the related art.

The switch 102 may control the current between the stimulating electrode 101 and the return electrode 103. The switch 102 may be connected between the stimulating electrodes 101 and the return electrode 103 to ground the stimulating electrodes 101 to the return electrode 103 in response to an on or off control signal.

FIG. 6 is a circuit diagram of the stimulating electrode 101 to which the switch 102 is connected. In FIG. 6, the conversion circuit for the current output from the photodiode and a stimulator may be replaced with a circuit configuration of the related art. The conversion circuit and the stimulator are not a gist of the present invention and are thus illustrated as a black box. Referring to FIG. 6, it can be seen that the switch 102 is connected to an output terminal in parallel in the circuit diagram of the stimulating electrode 101 of the related art.

The switch 102 allows an output line, through which an impulse of the stimulating electrode 101 is outputted, to branch to be connected to the return electrode 103. FIG. 6 illustrates the return electrode 103 as a ground. The switch 102 is provided as a plurality of switches 102, which may be connected to the stimulating electrodes 101, respectively. For example, the switches 102 are included in at least more than or equal to the number of the stimulating electrodes 101. As in FIG. 6, the switch 102 connects each of the arranged stimulating electrodes 101 to a single return electrode 103. The switch 102 operates the stimulating electrode 101 as the return electrode 103 according to an on or off state thereof. Thus, the subretinal prosthetic device 10 according to this embodiment allows the return electrode 103 to be disposed adjacent to the activated stimulating electrode 101 without being fixed.

In other words, a portion of the stimulating electrodes 101 adjacent to any one stimulating electrode 101 are operated as the return electrode 103. The adjacent stimulating electrodes referred to in the present specification refer to the portion of the plurality of stimulating electrodes spaced apart from the one stimulating electrode 101 at the same distances around the one stimulating electrode 101 for generating the active potential. For example, the portion of the array of the stimulating electrodes 101 outputs the active potential, and the remainder thereof is inactivated, in response to the external visual information. In this embodiment, when the portion of the stimulating electrodes 101 adjacent to the stimulating electrode 101 for outputting the active potential are converted into the return electrode 103, the current flowing from the activated stimulating electrode 101 does not stimulate an unintended bipolar cell therearound. Thus, it is noted that the portion of the stimulating electrodes 101 of this embodiment features the switch 102 connected thereto such that the portion of the stimulating electrodes 101 may be converted into the return electrode 103 in response to a control signal. Then, a method of controlling converting, into the return electrode 103, the portion of the stimulating electrodes adjacent to the activated stimulating electrode 101 is required. According to the requirement, the subretinal prosthetic device 10 according to this embodiment forms, as the scanning array 11, the portion of the stimulating electrodes adjacent to the one stimulating electrode 101. The portion of the stimulating electrodes 101 of the scanning array 11 may be spaced apart from a central stimulating electrode 101 thereof at the same distances. For example, when the central stimulating electrode 101 is activated, and the adjacent stimulating electrodes 101 spaced apart from the central stimulating electrode 101 at the same distances are converted into the return electrode 103, the current flowing into the return electrode 103 is the same as that flowing from the activated stimulating electrode 101, and thus the system may be stabilized. As a result, the adjacent stimulating electrodes may form a hexagonal array around the one stimulating electrode for generating the active potential. From the above description, those of ordinary skill in the art will appreciate that the stimulating electrodes are arranged around the central stimulating electrode to form the hexagonal array. For this reason, the stimulating electrodes 101 are arranged in the zigzag pattern on the at least one of the X- or Y-axis to be able to form the hexagonal array.

The control module 105 may set, as a scanning array, the portion of the stimulating electrodes included in a portion of a region in which the plurality of stimulating electrodes are arranged, switch from the portion of the plurality of stimulating electrodes of the scanning array 11 to the return electrode 103, and set, as the scanning array, another portion of the plurality of stimulating electrodes included in another portion of the region.

FIG. 7 illustrates a scanning array of the subretinal prosthetic device 10 according to an embodiment of the present invention. The scanning array 11 is set as the portion of stimulating electrodes 101 spaced apart from the one stimulating electrode 101 at the same distances to form the hexagonal array. Referring to FIG. 7, it is assumed that a central stimulating electrode 101(a) is activated. The hexagonal array, formed by six stimulating electrodes 101(b) around the central stimulating electrode 101(a), is referred to as the scanning array 11. As illustrated in FIG. 7, the scanning array 11 will be described with reference to a control state of the switch 102 connected to the stimulating electrodes 101. The control module 105 controls the switch 102 such that the switch 102 is turned on and that the stimulating electrodes 101(b) corresponding to the scanning array 11 are connected to the return electrode 103. Thus, all of the stimulating electrodes 101(b), corresponding to the scanning array 11, are operated as the return electrode 103. The on or off state of the switch 102 may be reversed according to a connection form. The central stimulating electrode 101(a) outputs the biphasic current by the conversion circuit 1011 of the stimulator, and the biphasic current is the active potential and stimulates rod and cone cells and/or a bipolar cell in a corresponding position. In this embodiment, the current outputted by the central stimulating electrode 101(a) flows into the return electrode 103 of the scanning array 11 adjacent thereto not to stimulate an unintended peripheral cell, which may prevent an image from blurring.

The control module 105 does not stationarily the scanning array 11. For example, the scanning array 11 can be understood as one electrode region moved or scanned from the entire region in which the stimulating electrodes 101 are arranged. The control module 105 gradually moves the scanning array 11 while turning on or off the stimulating electrodes 101 such that the stimulating electrodes 101 serves as the return electrode 103.

FIG. 8 is an example illustrating an operation of the scanning array 11 of the subretinal prosthetic device according to an embodiment of the present invention.

Referring to FIG. 8, the control module 105 as an example may move the scanning array 11 to the right in an X-axis direction on the substrate to scan a first row of the stimulating electrodes 101 and then may repeatedly move the scanning array 11 to the right in the X-axis direction from a second row thereof. Alternatively, the control module 105 may perform scanning in a Y-axis direction after the scanning of the first row. A pattern of the scanning performed by the control module 105 is sufficient to uniformly turn on or off the region of the arranged stimulating electrodes 101 and not limited to a specific pattern.

In this embodiment, it is noted that the control module 105 sets the scanning array 11 at a frequency of higher than or equal to 50 Hz. Referring to FIG. 8, a speed at which the scanning array 11 is moved is set to be higher than or equal to 50 Hz. In this embodiment, the user wearing the subretinal prosthetic device 10 may not recognize a turn-on or off conversion process of the scanning array 11. The control module 105 may move the scanning array 11 at a speed of 50 to 60 Hz. In FIG. 8, the user may not recognize the movement of the return electrode 103 moved at a speed of 50 to 60 Hz, which is a freeker-free frequency, and may recognize only an image corresponding to the shape "L."

FIG. 9 illustrates an arrangement of the stimulating electrode 101 and the return electrode 103 recognized by the user in the example of FIG. 8. As a result, the return electrode 103 scans the entire region in the form of the scanning array 11, and activate states of the return electrode 103 and the stimulating electrode 101 recognized by the user are as illustrated in FIG. 8. Referring to the electrode arrangement of FIG. 9, the return electrode 103 is disposed around the stimulating electrode 101. As a result, the current outputted by the activated stimulating electrode 101 is flowed into the return electrode 103 adjacent thereto and does not unnecessarily stimulate the other portion of the stimulating electrodes 101 included in the other portion of the region that may distort the shape "L."

The result predicted by the scanning method for the return electrode 103 using the hexagonal scanning array 11 is as illustrated in FIGS. 10 and 11. FIG. 10 illustrates an optical sensor array for a subretinal prosthetic device of the related art in which the return electrode 103 is formed stationarily. As in FIG. 10, it can be expected that even when the user is required to recognize an image having the shape "L," the image is distorted in the direction of the return electrode 103. In contrast, the subretinal prosthetic device 10 for variably scanning the return electrode 103 using a structure of the hexagonal scanning array 11 may stimulate the optic nerve 7 at a high resolution without significantly distorting the image having the shape "L" as in FIG. 11.

The control module 105 may perform control such that the same stimulating electrode 101 does not continue to be selected during the setting of the scanning array 11. The stimulating electrodes 101 of the scanning array 11 prevents the life of the element from being rapidly shortened while the stimulating electrodes 101 are turned on or off to serve as the return electrode 103. The reason is that when the stimulating electrodes 101 and the return electrode 103 are quickly and continuously turned on or off, the stimulating electrode 101 and the return electrode 103 may malfunction without responding to the turn-on or off.

In another embodiment of the present invention, a method of driving the above-mentioned subretinal prosthetic device 10 may include (a) setting the scanning array 11, (b) switching to the return electrode, and (c) moving the scanning array 11.

Operation (a) refers to setting, as the scanning array 11, the portion of the stimulating electrodes 101 included in the portion of the region in which the stimulating electrodes 101 are arranged, and the stimulating electrodes 101 are provided on the substrate under the retina to generate the active potential to the optic nerve 7 in response to the external visual information projected onto the retina.

Operation (a) sets, as the scanning array, the portion of the plurality of stimulating electrodes 101 spaced apart from any one of the plurality of stimulating electrodes 101 at the same distances around the one stimulating electrode 101, and the scanning array 11 may be the hexagonal array. Operation (b) refers to connecting the portion of the stimulating electrodes 101 of the scanning array 11 to the return electrode 103 for receiving the current. Operation (c) refers to setting, as the scanning array 11, the other portion of the stimulating electrodes 101 included in the other portion of the region in which the stimulating electrodes 101 are arranged. Operation (c) may set the scanning array 11 such that the other portion of the stimulating electrodes 101 selected in operation (a) do not continue to be selected. Operations (a) to (c) are repeated at a frequency of higher than or equal to 50 Hz. The driving method of operations (a) to (c) refers to the operations performed by the above-mentioned control module 105.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. Therefore, the scope of the present invention should not be limited to the above-described embodiments, but should be determined by all changes or modifications derived from the scope of the accompanying claims and equivalents thereof.

What is claimed is:

1. A subretinal prosthetic device comprising:
a substrate provided under a retina;
a return electrode for receiving a current such that a ground is formed on the substrate;
each of a plurality of photodiodes for outputting a dark current in response to external visual information projected onto the retina;
a plurality of conversion circuits connected to the plurality of photodiodes, respectively, and for converting and outputting the dark current;
a plurality of stimulating electrodes provided on the substrate and for generating an active potential to an optic nerve on the basis of the converted dark current; and
a plurality of switches formed between each of the plurality of stimulating electrodes and the return electrode,
wherein the subretinal prosthetic device activates a first stimulating electrode of the plurality of stimulating electrodes on the basis of the external visual information and turns on the plurality of switches formed between a plurality of second stimulating electrodes, which are adjacent to the first stimulating electrode of the plurality of stimulating electrodes, and the return electrode to ground the plurality of second stimulating electrodes, and
wherein the substrate further comprises a control module for setting, as a scanning array, a portion of the plurality of stimulating electrodes included in a portion of a region in which the plurality of stimulating electrodes are arranged, switching from the portion of the plurality of stimulating electrodes of the scanning array to the return electrode, and setting, as the scanning array, another portion of the plurality of stimulating electrodes included in another portion of the region.

2. The subretinal prosthetic device as set forth in claim 1, wherein the substrate has the plurality of stimulating electrodes arranged in a zigzag pattern in an X- or Y-axis column.

3. The subretinal prosthetic device as set forth in claim 1, wherein the stimulating electrode outputs a biphasic current having two phases of a negative pole and a positive pole for balancing of an electric charge transferred to the optic nerve.

4. The subretinal prosthetic device as set forth in claim 1, wherein each of the switches allows an output line, through which an impulse of the stimulating electrode is outputted, to branch to be connected to the return electrode.

5. The subretinal prosthetic device as set forth in claim 1, wherein each of the switches is provided as a plurality of switches, which are connected to the plurality of stimulating electrodes, respectively.

6. The subretinal prosthetic device as set forth in claim 1, wherein the substrate allows a portion of the plurality of stimulating electrodes, which are adjacent to any one of the plurality of stimulating electrodes for generating an active potential, to be operated as the return electrode.

7. The subretinal prosthetic device as set forth in claim 6, wherein the adjacent stimulating electrodes are the portion of the plurality of stimulating electrodes spaced apart from the one stimulating electrode at the same distances around the one stimulating electrode for generating the active potential.

8. The subretinal prosthetic device as set forth in claim 6, wherein the adjacent stimulating electrodes form a hexagonal array around the one stimulating electrode for generating the active potential.

9. The subretinal prosthetic device as set forth in claim 1, wherein the control module sets the scanning array at a frequency of higher than or equal to 50 Hz.

10. The subretinal prosthetic device as set forth in claim 1, wherein the scanning array is set as the portion of the plurality of stimulating electrodes spaced apart from any one of the plurality of stimulating electrodes at the same distances around the one stimulating electrode to form a hexagonal array.

11. The subretinal prosthetic device as set forth in claim 1, wherein the control module performs control such that the same stimulating electrode does not continue to be selected during the setting of the scanning array.

12. A method of driving a subretinal prosthetic device comprising: a substrate provided under a retina; a return electrode for receiving a current such that a ground is formed on the substrate; a plurality of photodiodes; a plurality of conversion circuits connected to the plurality of photodiodes, respectively; a plurality of stimulating electrodes provided on the substrate and connected to the plurality of conversion circuits, respectively; and a plurality of switches formed between each of the plurality of stimulating electrodes and the return electrode, the method comprising:
allowing each of the plurality of photodiodes to output a dark current in response to external visual information projected onto the retina;
allowing the plurality of conversion circuits to convert and output the dark current; and
allowing the plurality of stimulating electrodes to generate an active potential to an optic nerve on the basis of the converted dark current, wherein the generating of the active potential comprises:
(a) setting, as a scanning array, a portion of the plurality of stimulating electrodes included in a portion of a region in which the plurality of stimulating electrodes for generating the active potential are arranged and activating a first stimulating electrode of the portion of the plurality of stimulating electrodes set as the scanning array;

(b) turning on the plurality of switches formed between a plurality of second stimulating electrodes, which is adjacent to the first stimulating electrode of the portion of the plurality of stimulating electrodes, and the return electrode to ground the plurality of second stimulating electrodes; and (c) setting, as the scanning array, another portion of the plurality of stimulating electrodes included in another portion of the region in which the plurality of stimulating electrodes are arranged, wherein operations (a) to (c) are repeated at a frequency of higher than or equal to 50 Hz.

13. The method as set forth in claim 12, wherein operation (a) sets, as the scanning array, the portion of the plurality of stimulating electrodes spaced apart from any one of the plurality of stimulating electrodes at the same distances around the one stimulating electrode, and the scanning array is a hexagonal array.

14. The method as set forth in claim 12, wherein operation (c) sets the scanning array such that the portion of the plurality of stimulating electrodes selected in operation (a) do not continue to be selected.

* * * * *